United States Patent
Goldmann

(10) Patent No.: US 8,313,533 B2
(45) Date of Patent: Nov. 20, 2012

(54) SHEATHING FOR RESTORING THE FUNCTION OF VALVES OF VARICOSE VEINS AND USE OF THE SHEATHING IN SURGERY

(75) Inventor: Helmut Goldmann, Tuttlingen/Donau (DE)

(73) Assignee: Aesculap AG (DE)

( * ) Notice: Subject to any disclaimer, the term of this patent is extended or adjusted under 35 U.S.C. 154(b) by 819 days.

(21) Appl. No.: 12/328,852

(22) Filed: Dec. 5, 2008

(65) Prior Publication Data

US 2009/0149937 A1 Jun. 11, 2009

(30) Foreign Application Priority Data

Dec. 10, 2007 (DE) .................... 10 2007 061 301

(51) Int. Cl.
*A61F 2/02* (2006.01)
(52) U.S. Cl. .................................................. 623/23.72
(58) Field of Classification Search .................. 606/153, 606/155; 623/1.13, 1.37, 1.44, 1.49, 1.5, 623/1.54, 23.72
See application file for complete search history.

(56) References Cited

U.S. PATENT DOCUMENTS

| 4,904,254 A | 2/1990 | Lane |
| 5,147,389 A | 9/1992 | Lane |
| 5,163,951 A * | 11/1992 | Pinchuk et al. ................. 600/36 |
| 6,447,551 B1 | 9/2002 | Goldmann |
| 6,610,006 B1 * | 8/2003 | Amid et al. ..................... 600/37 |
| 2002/0026092 A1 * | 2/2002 | Buckberg et al. ............... 600/37 |
| 2004/0215309 A1 | 10/2004 | Moritz et al. |

FOREIGN PATENT DOCUMENTS

| DE | 3318730 | 11/1984 |
| DE | 3643465 | 7/1988 |
| DE | 4107284 | 9/1991 |
| DE | 199 10 340 | 9/2000 |
| DE | 199 12 648 A1 | 9/2000 |
| EP | 1 561 437 | 8/2005 |
| EP | 2006/072926 | 7/2006 |
| WO | 88/00454 | 1/1988 |
| WO | 95/05122 | 2/1995 |
| WO | 97/40755 | 11/1997 |
| WO | 02/076305 | 10/2002 |
| WO | 03/011190 | 2/2003 |
| WO | 2004/026178 A2 | 4/2004 |

OTHER PUBLICATIONS

B. Geier et al., "Extraluminale Valvuloplastie bei Stamminsuffizienz der V. saphena magna", 2004, vol. 33, pp. 149-155, *Phlebologie*.
Seshadri Raju, M.D., Venous Insufficiency of the Lower Limb and Stasis Ulceration, 1982, pp. 688-696, *Changing Concepts and Management*.

* cited by examiner

*Primary Examiner* — Ryan Severson
(74) *Attorney, Agent, or Firm* — DLA Piper LLP (US)

(57) ABSTRACT

A sheathing has a longitudinal direction and a transverse direction for restoring function of venous valves of varicose veins in the form of a planar, flexible piece of material, wherein the piece of material includes a nonwoven material.

26 Claims, 1 Drawing Sheet

SHEATHING FOR RESTORING THE FUNCTION OF VALVES OF VARICOSE VEINS AND USE OF THE SHEATHING IN SURGERY

RELATED APPLICATION

This application claims priority of German Patent Application No. 102007061301.8, filed Dec. 10, 2007, herein incorporated by reference.

TECHNICAL FIELD

This disclosure relates to a sheathing for restoring the function of valves of varicose veins and to the use thereof in surgery.

BACKGROUND

Chronic venous insufficiency of the lower extremities is a disorder which is widespread in the population. The cause thereof is frequently an impaired function of venous valves. Recent investigations demonstrate that the pathogenesis of varicose veins is causally connected to altered elastic properties within the vessel wall leading to dilatation of the vein wall. As a result of the dilatation, the venous valves are no longer able to close, leading to an increased reflux of blood into the affected veins and finally to the development of varicosis. In particular, non-closure of the terminal valve of the great saphenous vein (GSV) is frequently the starting point of primary varicosis.

The range of possible therapies for incompetence of the trunk of the great saphenous vein extends from conservative measures such as, for instance, compression stockings, physio- and pharmacotherapy, via minimally invasive procedures to surgical procedures. Conventional surgical treatment consists of removing (stripping) the incompetent veins. However, very recently, minimally invasive procedures such as, for example, endovascular laser therapy (ELT) and radiofrequency obliteration (RFO) have increasingly been used. One disadvantage of the surgical and minimally invasive procedures is, however, that the relevant veins are respectively removed from the body and obliterated in the body.

The general desire to retain venous bypass material for coronary bypass surgery, and the objective of minimizing surgical trauma have led to the development of various vein-retaining surgical procedures. Particular mention should be made in this connection of so-called "extraluminal valvuloplasty" of the GSV terminal valve. Function of the valve is restored in that method of treatment by placing a cuff around the dilated valve region. It is possible by that surgical technique to eliminate pathological refluxes into the veins of the lower extremities without removing the veins themselves. Examples of such cuffs are disclosed in WO 88/00454 A1, U.S. Pat. No. 5,147,389, U.S. Pat. No. 4,904,254 and WO 02/076305 A1. However, the disadvantages of the cuffs described therein are, besides the elaborate and therefore costly manner of their manufacture, especially the fact that the cuffs described therein consist of materials with low or zero extensibility, and thus the cuff does not have extensibility appropriate for the vein.

A comparatively simple vein cuff made of Dacron® (polyethylene terephthalate) has been successfully employed by Mumme et al. (Phlebologie 2004; 33: 149 to 155) for extraluminal venous valve reconstruction in clinical studies. However, a problem with this cuff material too is that it has little elastic extensibility. It is moreover generally known that the Dacron® may induce foreign-body reactions, especially fibrotic reactions (S. Raju, ANN. SURG. (1983) 197, 688 to 697).

It could therefore be helpful to provide a sheathing for varicose veins which overcomes the known problems. The sheathing is intended in particular to have elasticity appropriate for veins and be biocompatible and able to be manufactured easily and at low cost.

SUMMARY

I provide a sheathing having a longitudinal direction and a transverse direction for restoring function of venous valves of varicose veins in the form of a planar, flexible piece of material, wherein the piece of material includes a nonwoven material.

BRIEF DESCRIPTION OF THE DRAWINGS

Further details and features are evident from the following description of preferred constructions on the basis of the figures. Individual features can be implemented alone or in combination with other features in these constructions. All the figures are hereby made contents of this description by express reference.

The figures show the following.

DETAILED DESCRIPTION

Figure 1:
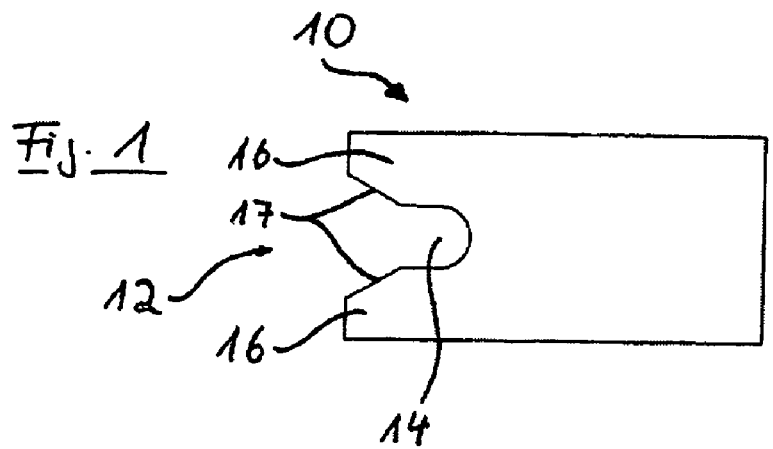
FIG. 1 is a side view of a construction of a sheathing.

It will be appreciated that the following description is intended to refer to specific examples of structure selected for illustration in the drawings and is not intended to define or limit the disclosure, other than in the appended claims.

I therefore provide a sheathing having a longitudinal direction and a transverse direction for restoring the function of valves of varicose veins in the form of a planar, flexible piece of material, where the piece of material includes a nonwoven material.

I provide a sheathing or a vein patch or a vein cuff for venous valve reconstruction for varicose veins in human and/or veterinary medicine. The sheathing is particularly suitable for terminal valve reconstruction of a varicose great saphenous vein. As already mentioned, incompetence of the trunk of the great saphenous vein is in most cases the etiological starting point for the development of primary varicosis. To restore intact closure of venous valves, the sheathing may be advantageously placed in the manner of a cuff around the varicose vein. The cuff acts as a type of internal compression stocking which preferably completely sheaths the relevant section of vein. While continuously monitoring the blood reflux, in most cases via a lateral venous branch which is not ligated, it is possible to constrict the cuff, and thus the diameter of the lumen of the vein, continuously until blood reflux into the vein is no longer detectable. The sheathing is then fastened on its edges which are in contact or, where appropriate, overlapping. The edges can be, for example, bonded and/or sutured.

In one construction, the length of the piece of material is greater than its width. The piece of material itself may in particular be in the form of strips. It is possible in principle for the piece of material to have fastening elements, for example, straps for fastening the sheathing to a vein. The fastening elements are preferably shank-like projections of the piece of material, the piece of material preferably having two shank-like projections. The fastening elements can be provided in particular for fastening the sheathing in the area of a natural vein junction region, for example, the so-called "arch region." The arch region is the natural vein junction of the leg vein great saphenous vein with the lower-lowering femoral vein (also referred to as "Vena femoralis"). To restore the function of the valve of a varicose great saphenous vein, the sheathing is usually fastened to the femoral vein. Suitable fastening methods are all fastening techniques familiar to the skilled worker, for example bonding and/or suturing.

In another construction, the piece of material has an approximately rectangular shape and has on a narrow side a specific cutout. This cutout is particularly advantageously designed such that the sheathing can be placed in the area of a natural vein junction region. The specific cutout is preferably a U-shaped cutout whose width is preferably adapted to the diameter of the vein to be enveloped. The U-shaped cutout preferably has a width between about 5.8 and about 8.2 mm, especially a width of about 6 mm.

In a further construction, the piece of material is adapted in its dimensions to the varicose vein of which the function of the valve is to be restored. The piece of material may have a length of between about 3 and about 5 cm, preferably of about 4 cm, and a width of between about 1 and about 3 cm, preferably of about 2 cm.

The piece of material is moreover preferably designed to be extensible, in particular substantially elastic. It is particularly advantageous for the piece of material to have an extensibility which substantially corresponds to the extensibility of healthy veins, in particular an intact great saphenous vein. The extensibility of healthy or intact veins is also referred to as "compliance."

It is particularly preferred for the piece of material, in particular the nonwoven material, to be prestretched in the transverse direction. The prestretching particularly advantageously results in the piece of material acquiring a pressure-extension behavior which preferably corresponds approximately to the extensibility of intact veins. Prestretching of the nonwoven material of the sheathing in the transverse direction may advantageously lead to a strengthening and thus stabilization of the sheathing. The reason for this is in particular the realignment of the fibers of the nonwoven material. The prestretching, comparable with a cold orientation, results in the fibers losing at least part of their original orientation relative to one another and are realigned. The fiber realigning may lead to a strengthening of the nonwoven material and thus overall of the sheathing. The piece of material is normally prestretched cold.

The piece of material, in particular the nonwoven material, is preferably prestretched mechanically. In a further construction, the piece of material is prestretched in the transverse direction by a tensile force of between about 1 and about 20 N/cm, in particular about 4 and about 18 N/cm, preferably about 8 and about 16 N/cm.

The nonwoven material is normally a web. The nonwoven material is preferably in the form of a sprayed web. It is possible to provide for the web, in particular a sprayed web, to have fibers which are bonded together. Normally a solution of the nonwoven material in a volatile solvent is used to manufacture the web. Suitable solvents are in particular halogenated solvents. The solvents may in this connection be partially halogenated and/or perhalogenated. Chlorinated and/or fluorinated solvents are particularly preferred, for example chloroform and/or dichloromethane. A sprayed web structure is produced by spraying the solution of the nonwoven material ordinarily onto a flat application surface. The spraying itself normally takes place with the aid of a suitable spraying or atomizing device, for example a spray gun or nozzle. The dimensions of the spraying path in this case are such that fibers of the nonwoven material are formed from the solution on traveling along the spraying path. The spraying path may, for example, amount to between about 10 and about 75 cm, in particular about 15 and about 20 cm. On the other hand, the solvent is ordinarily volatilized on traveling along the spraying path so that nonwoven material fibers are deposited on the application surface and, owing to a certain residual moisture, are bonded together preferably to form a three-dimensional fiber structure (web structure). A particular advantage of the sprayed web technique is that the average pore diameter in the sprayed web can be adjusted as a function of the spraying path. A longer spraying path results in a larger average pore diameter in the finished sprayed web. It is possible in this way to produce web structures with pore gradients.

In a further construction, the nonwoven material is configured as film or sheet. The sheet may be in particular a cast or sprayed sheet. The cast sheet can be produced, for example, by pouring a solution of the nonwoven material over a suitable support plate. The cast sheet is obtained after the solvent has volatilized and/or where appropriate after one or more drying steps. The sprayed sheet can be produced by a process corresponding to the sprayed web technique described in the previous section, with the dimensions of the spraying path now being such that it is not possible for fibers of the nonwoven material to form from the solution on traveling along the spraying path. The spraying path may be, for example, between about 1 and about 10 cm, in particular about 4 and about 8 cm. For further details and features, reference is made to the previous description.

In a further construction, the piece of material has a multilayer, in particular bi- or trilayer structure. It is possible, for example, for the piece of material to be composed in total of three layers, of which two layers are in the form of web structures, and the third layer is configured as film or sheet. The film- or sheet-like layer is preferably disposed in sandwich fashion between the two web structures.

The nonwoven material may furthermore have fibers with a fiber thickness of between about 0.01 and about 20 μm, in particular about 0.1 and about 10 μm, preferably about 0.5 and about 5 μm.

In a further construction, the nonwoven material is a polymer which is substantially non-absorbable under physiological conditions. The nonwoven material is preferably a biocompatible polymer. The nonwoven material is preferably a polyurethane. Polyurethane has the advantage that it represents an extremely biocompatible material which moreover has an elastic extensibility which substantially corresponds to the natural extensibility of a healthy vein wall. I provide in particular for the nonwoven material to be a thermoplastic polyurethane. The polyurethane is expediently soluble in organic solvents, especially in volatile organic solvents. The nonwoven material is in particular a linear polyurethane, preferably linear aliphatic polyurethane. Suitable polyurethanes may be in particular polyurethanes which are prepared from macromolecular and/or low molecular weight aliphatic diols and aliphatic diisocyanates. I provide in particular for the macromolecular diols to be polycarbonates, in particular 1,6-hexanediol polycarbonate. Suitable and preferred low molecular weight diols are 2,2,4-trimethylhexanediol, 2,4,4-trimethylhexanediol and/or 1,4-butanediol. The aliphatic diisocyanates preferably used are cycloaliphatic diisocyanates, in particular 4,4'-dicyclohexylmethane diisocyanate and/or 1,4-cyclohexyl diisocyanate. Concerning further suitable polyurethanes, reference is made to DE 36 43 465 A1, DE 33 18 730 A1 and DE 41 07 284 A1, the disclosure of which is incorporated herein by reference.

The nonwoven material may further be a polyurethane having a molecular weight of between about 5000 and about 50 000 daltons, in particular about 20 000 and about 40 000 daltons.

In a particularly advantageous construction, the piece of material is designed to be thinner than known cuffs. The piece of material preferably has a thickness which allows the sheathing to be fastened without problems, in particular by suturing to a natural vein. The piece of material preferably has a thickness of between about 0.1 and about 0.5 mm, in particular about 0.15 and about 0.3 mm. A piece of material which is thin and, in particular, designed to be elastically extensible moreover particularly advantageously improves the general manipulation by the surgeon, it thus being possible to reduce operation times and risks.

The piece of material may be porous. The piece of material may in particular be porous throughout. The piece of material preferably has pores having a diameter of between about 0.1 and about 100 μm, in particular about 0.5 and about 50 μm, preferably about 1 and about 10 μm.

It is possible for the sheathing to have at least one reinforcement. The reinforcement may be, for example, a textile net, a metal wire or a sheet. The reinforcement is preferably adapted to the compliance of natural healthy veins.

It is moreover possible for the sheathing to include active substances, in particular antimicrobial active substances. The active substances themselves may moreover be present in the form of particles whose diameter is preferably between about 50 and about 100 nm. The active substance particles may also be combined to give agglomerates. The size of the agglomerates can be in particular between about 5 and about 10 μm. Suitable active substances are in particular metals or metal alloys having an antimicrobial effect, with particular preference for metallic silver.

It is possible to apply the active substances where appropriate together with other materials in the form of a layer on the sheathing. The active substances may, for example, be present in the form of an absorbable layer on the surface of the sheathing together with absorbable materials, in particular gelatin and/or collagen. The sheathing particularly preferably has a silver layer. The thickness of the silver layer may in principle be in the range between about 1000 and about 4000 Å, in particular about 1000 and about 2500 Å.

In a further construction, the sheathing is in packaged form. The sheathing is particularly advantageously sterilizable and is preferably in sterilized form.

The piece of material may consist of the nonwoven material. Concerning further details and features of the nonwoven material, reference is made to the previous description.

I further provide a kit, in particular for use in extraluminal valvuloplasty, which comprises at least the sheathing. The kit preferably comprises as a further component a biocompatible adhesive composition. The adhesive composition itself may include, for example, of n-alkyl cyanoacrylates. The adhesive composition preferably consists of n-butyl-2-cyanoacrylate (Histoacryl®). As alternative to an adhesive composition or in combination therewith, the kit may include a suture material, for example, a polypropylene thread.

I also provide for use of the sheathing for the provision or production of a surgical implant for restoring the function of the venous valves of varicose veins, in particular of a varicose great saphenous vein. The sheathing is in this connection particularly suitable for use in extraluminal valvuloplasty.

FIG. 1 shows a sheathing 10 which is configured completely as a porous sprayed web. The sprayed web material is a polyurethane such as a polyester carbonate urethane. The sheathing 10 is a rectangular piece of material about 4×2 cm in size, one narrow side 12 of which has a U-shaped cutout 14, and the sheathing 10 thus acquires two shank-like projections 16. The width of the cutout 14 is about 6 mm. The narrow side 12 additionally has slopes 17 which are beveled in the direction of the U-shaped cutout 14. This specific cutout makes it possible to place the sheathing 10, for example, accurately in the terminal valve region of an incomplete great saphenous vein (GSV), especially in the angle between the GSV junction and the lower-lying femoral vein (concerning this, cf. also the arch region depicted in FIG. 2). The thickness of the sheathing 10 is about 0.15 mm. It is thus possible for the sheathing 10 to be sutured particularly easily in the area of a natural vein junction region, especially with the femoral vein.

Figure 2:
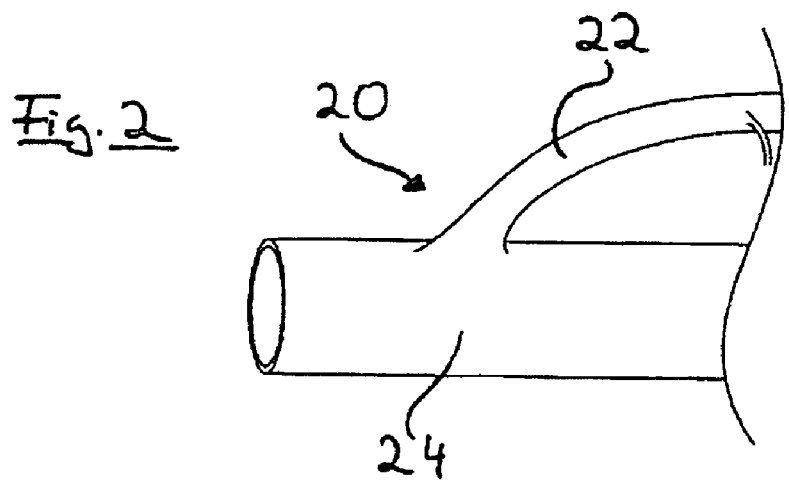
FIG. 2 is a perspective view of the arch region.

FIG. 2 shows diagrammatically the natural junction region 20 of the great saphenous vein (GSV) 22 with the lower-lying leg vein femoral vein 24. The junction region 20 is also referred to as arch region. The venous valve of the great saphenous vein 22 is approximately located where the GSV 22 joins the lower-lying femoral vein 24. If the function of the valve of the great saphenous vein 22 is impaired, usually because the venous flaps of the valve no longer close, there is an increased blood reflux into the great saphenous vein 22. This results in an increased stasis of blood in the lower extremities, and thus the blood pressure and therefore generally the risk of varicosis increases.

Figure 3:
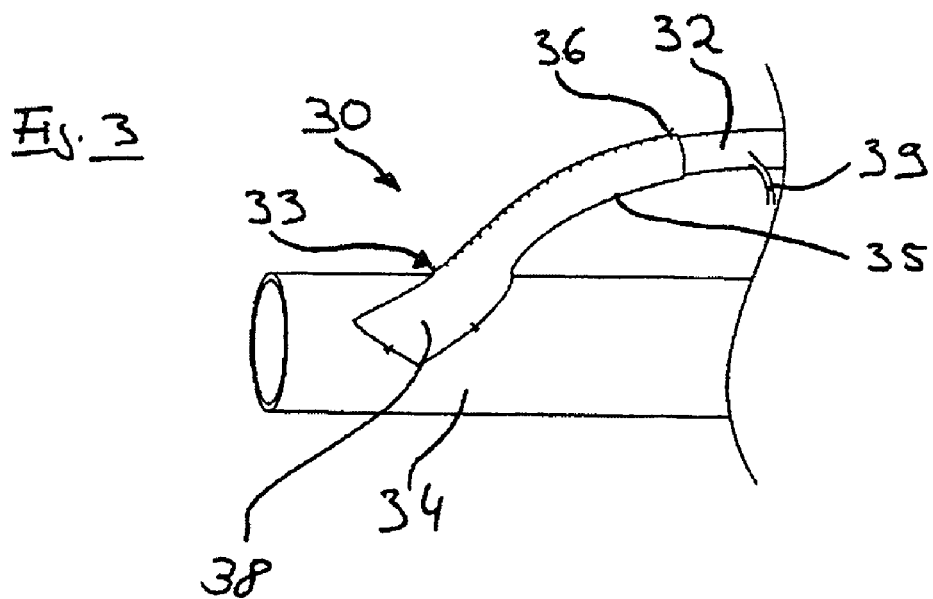
FIG. 3 is a perspective view of the terminal valve region of the great saphenous vein after performance of an extraluminal valvuloplasty.

FIG. 3 shows diagrammatically the arch region 30 after performance of an extraluminal valvuloplasty as is known in a similar manner for a polyester sheathing. The sheathing 35 composed of a polyurethane web is substantially completely wound around the great saphenous vein 32 starting from its junction 33 with the underlying femoral vein 34 over a particular length segment. The sheathing 35 is sutured with a polypropylene thread 36 at its edges which are in contact or where appropriate overlapping. The sheathing 35 is also sutured via two shank-like projections 38 to the femoral vein 34. The non-ligated side branch 39 serves as indicator vein for monitoring the blood reflux during the constriction of the diameter of the lumen of the great saphenous vein by means of the sheathing 35.

Although the apparatus and methods have been described in connection with specific forms thereof, it will be appreciated that a wide variety of equivalents may be substituted for the specified elements described herein without departing from the spirit and scope of this disclosure as described in the appended claims.

The invention claimed is:

1. A sheathing having a longitudinal direction and a transverse direction comprising a planar, flexible piece of material including a nonwoven material that restores functionality of venous valves of varicose veins, wherein the piece of material has an approximately rectangular shape and has on one narrow side a U-shaped cutout, wherein the U-shaped cutout is along the longitudinal direction and an opposing edge is perpendicular to the longitudinal direction.

2. The sheathing of claim 1, having a length of the piece of material greater than its width.

3. The sheathing of claim 1, wherein the piece of material has two shank-like projections.

4. The sheathing of claim 1, wherein the piece of material is extensible.

5. The sheathing of claim 1, wherein the piece of material has an extensibility which substantially corresponds to the extensibility of healthy veins.

6. The sheathing of claim 1, wherein the piece of material is prestretched in a transverse direction.

7. The sheathing of claim 1, wherein the piece of material is prestretched in a transverse direction by a tensile force of between about 1 and about 20 N/cm.

8. The sheathing of claim 1, wherein the piece of material is prestretched in a transverse direction by a tensile force of between about 4 and about 18 N/cm.

9. The sheathing of claim 1, wherein the piece of material is prestretched in a transverse direction by a tensile force of between about 8 and about 16 N/cm.

10. The sheathing of claim 1, wherein the nonwoven material is in the form of a sprayed web.

11. The sheathing of claim 10, wherein the sprayed web has fibers which are bonded together.

12. The sheathing of claim 1, wherein the nonwoven material is configured as a film or a sheet.

13. The sheathing of claim 1, wherein the piece of material has a bi- or trilayer, structure.

14. The sheathing of claim 1, wherein the nonwoven material has fibers with a fiber thickness of between about 0.01 and about 20 µm.

15. The sheathing of claim 1, wherein the nonwoven material has fibers with a fiber thickness of between about 0.1 and about 10 µm.

16. The sheathing of claim 1, wherein the nonwoven material has fibers with a fiber thickness of between about 0.5 and about 5 µm.

17. The sheathing of claim 1, wherein the nonwoven material is a polymer which is substantially non-absorbable under physiological conditions.

18. The sheathing of claim 1, wherein the nonwoven material is a linear aliphatic polyurethane.

19. The sheathing of claim 1, wherein the nonwoven material is a polyurethane having a molecular weight of between about 5000 and about 50000 daltons.

20. The sheathing of claim 1, wherein the nonwoven material is a polyurethane having a molecular weight of between about 20000 and about 40000 daltons.

21. The sheathing of claim 1, wherein the piece of material has a thickness of between about 0.1 and about 0.5 mm.

22. The sheathing of claim 1, wherein the piece of material has a thickness of between about 0.15 and about 0.3 mm.

23. The sheathing of claim 1, wherein the piece of material is porous.

24. The sheathing of claim 1, wherein the sheathing has a reinforcement.

25. The sheathing of claim 1, wherein the piece of material consists of the nonwoven material.

26. A kit, for use in extraluminal valvuloplasty, comprising at least one sheathing of claim 1 and a biocompatible adhesive composition for the sheathing.

* * * * *